(12) United States Patent
Neukermans

(10) Patent No.: US 6,561,231 B2
(45) Date of Patent: May 13, 2003

(54) METHOD FOR FILLING ACOUSTIC IMPLANTABLE TRANSDUCERS

(76) Inventor: Armand P. Neukermans, 4 Horseshoe Bend, Portola Valley, CA (US) 94028

( * ) Notice: Subject to any disclaimer, the term of this patent is extended or adjusted under 35 U.S.C. 154(b) by 0 days.

(21) Appl. No.: 10/057,388

(22) Filed: Jan. 25, 2002

(65) Prior Publication Data

US 2002/0062875 A1 May 30, 2002

Related U.S. Application Data

(63) Continuation-in-part of application No. 09/688,292, filed on Oct. 13, 2000.
(60) Provisional application No. 60/159,154, filed on Oct. 13, 1999.

(51) Int. Cl.[7] .................................................. B65B 1/04
(52) U.S. Cl. .................................. 141/4; 141/8; 141/51; 141/82
(58) Field of Search ............................... 141/4, 5, 6, 7, 141/8, 47–50, 51, 82, 98, 234, 237; 600/25

(56) References Cited

U.S. PATENT DOCUMENTS

| 5,564,479 A | 10/1996 | Yoshihara |
| 5,601,125 A | 2/1997 | Parsoneault et al. |
| 6,199,600 B1 | 3/2001 | Ahn et al. |

*Primary Examiner*—Steven O. Douglas
(74) *Attorney, Agent, or Firm*—D. E. Schreiber

(57) ABSTRACT

Methods for filling transducers of a fully implantable hearing aid system with liquids having either a high or a low vapor pressure are described. Methods are also described for avoiding damage to transducers during their testing and shipment.

5 Claims, 4 Drawing Sheets

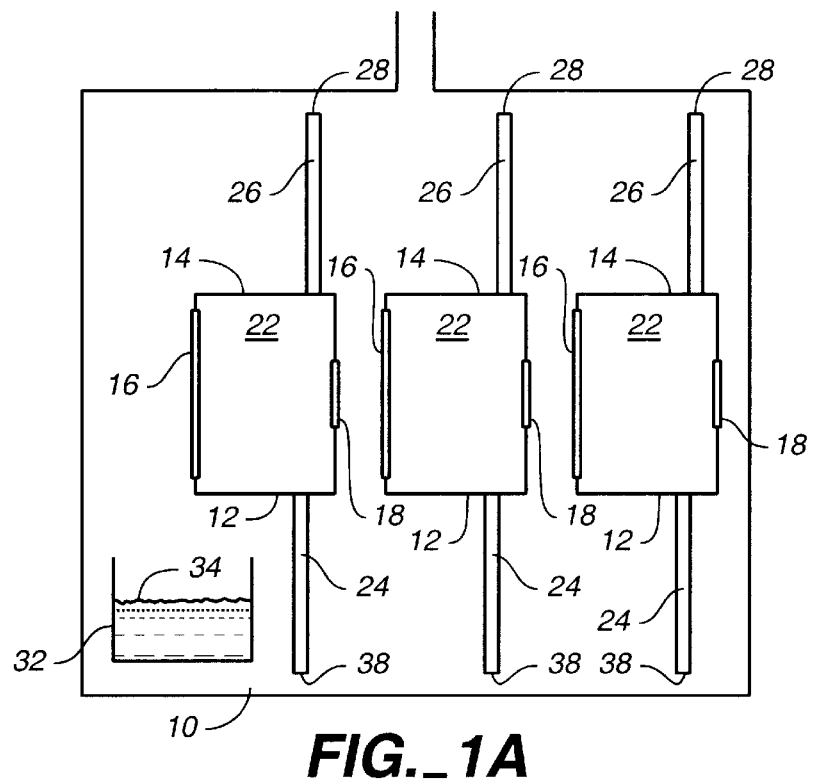
FIG._1A
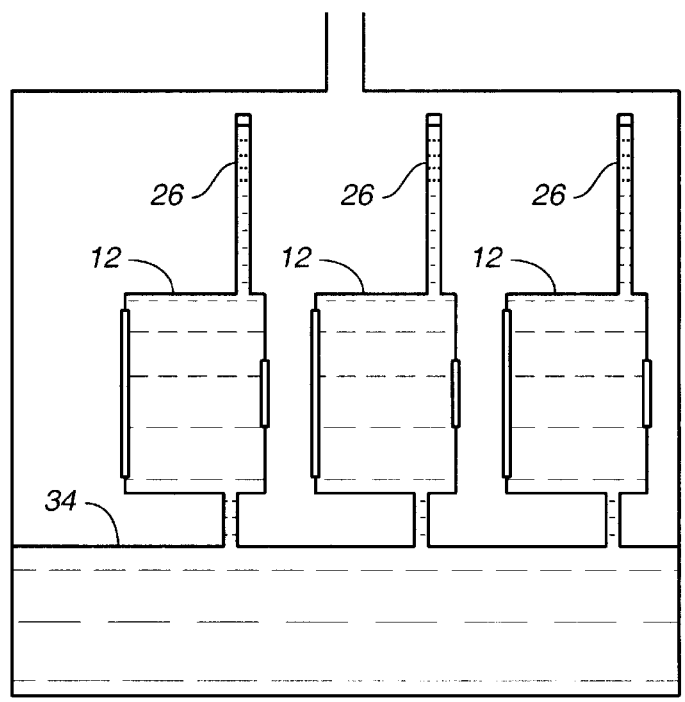
FIG._1B

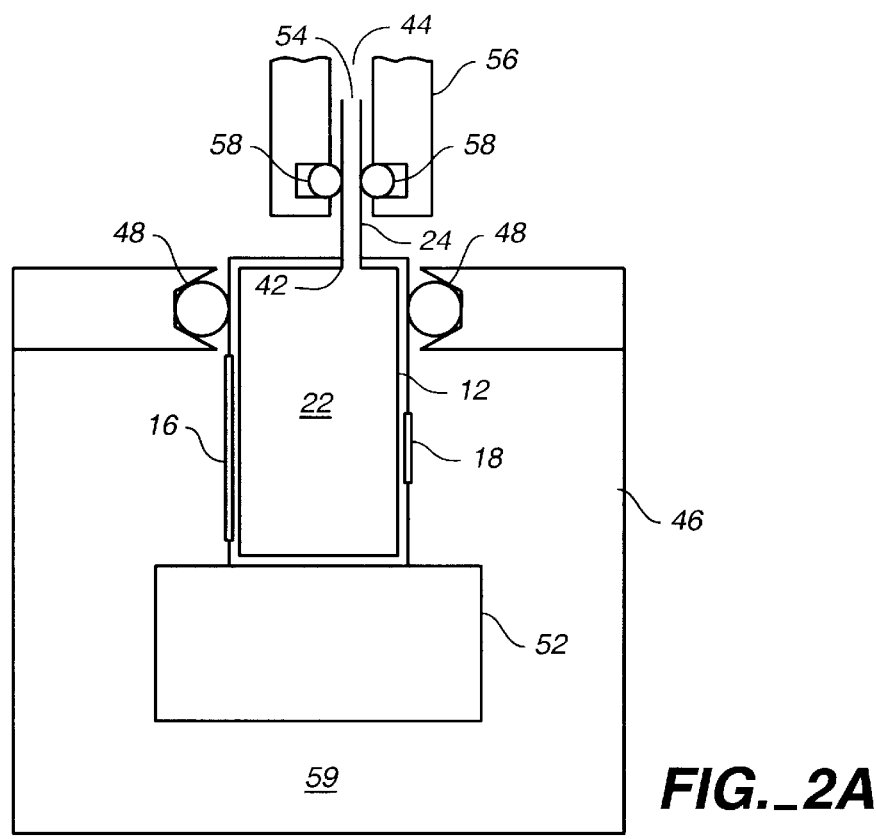
FIG._2A
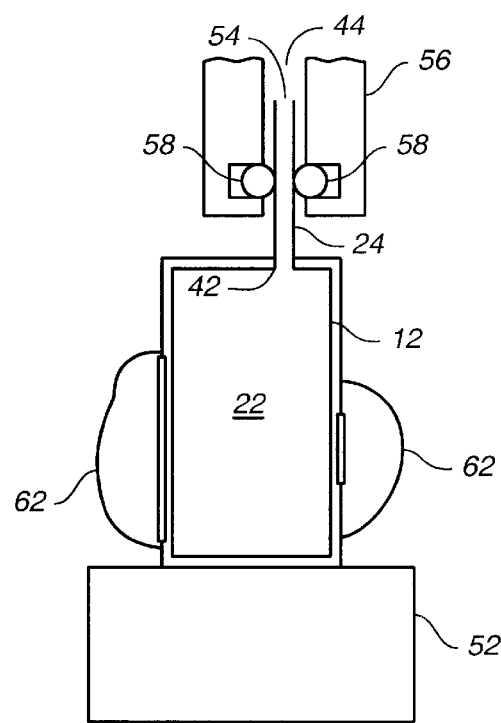
FIG._2B

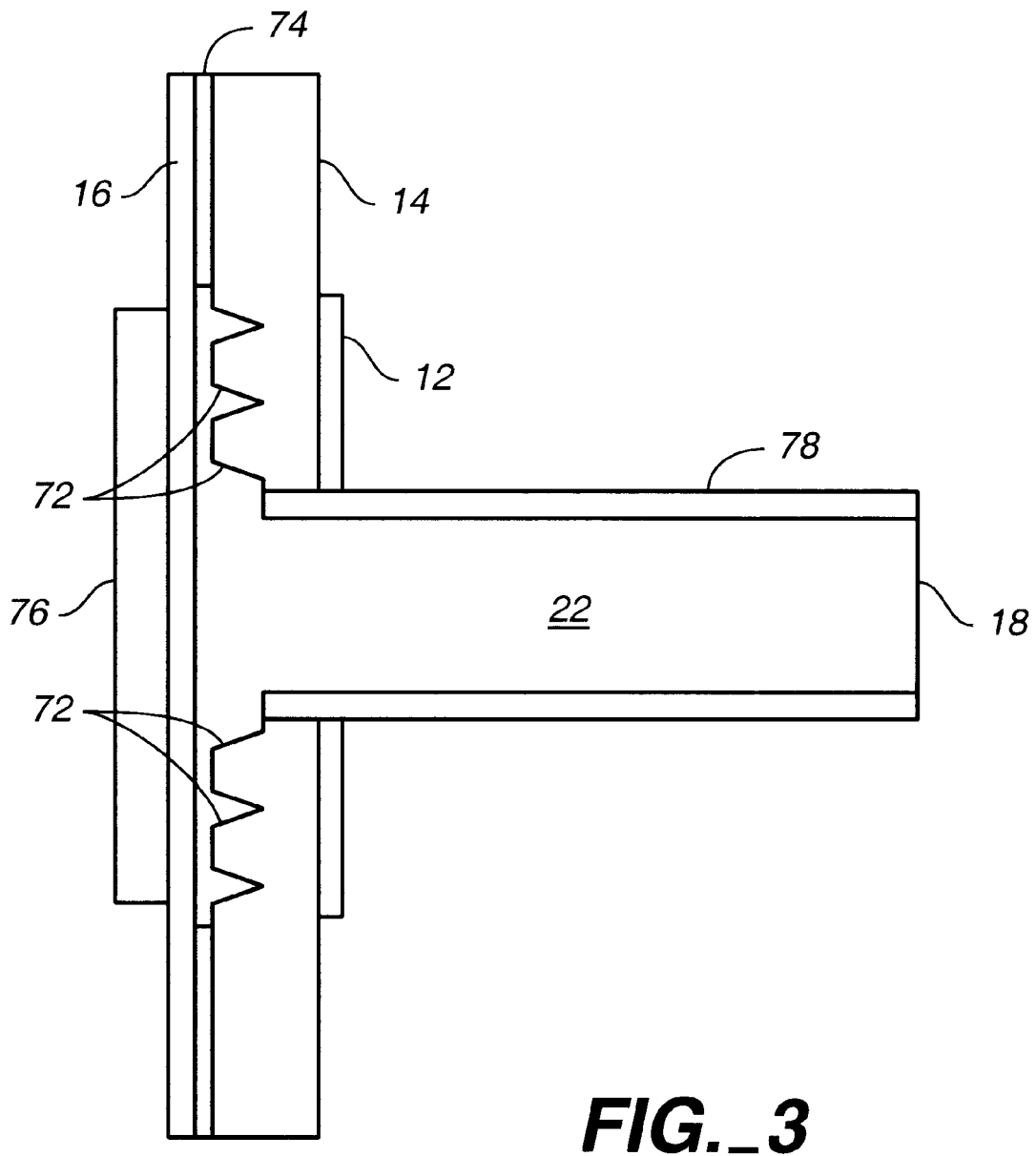
FIG._3

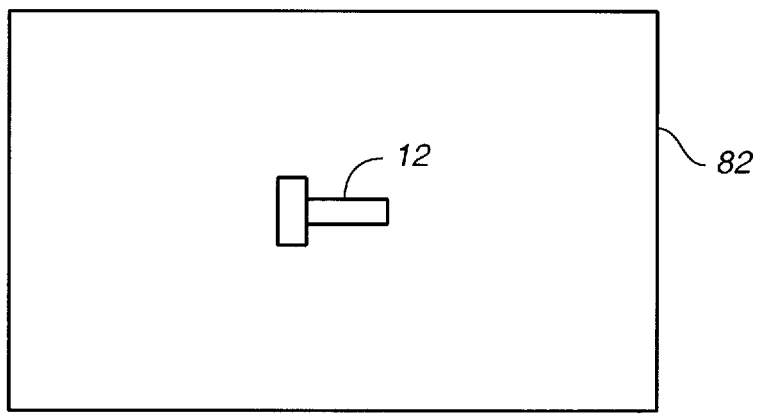
FIG._4
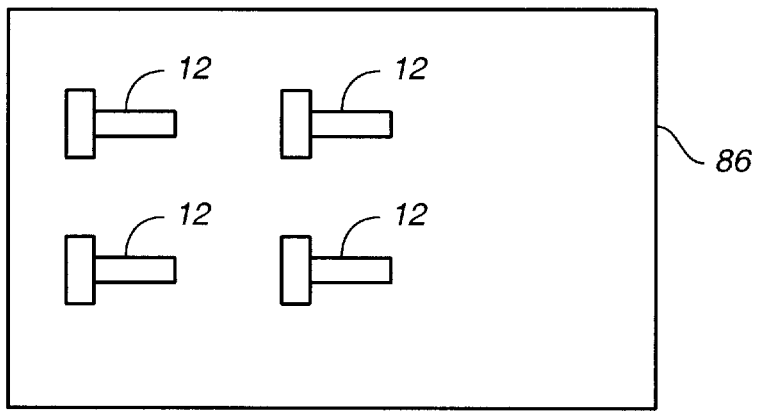
FIG._5
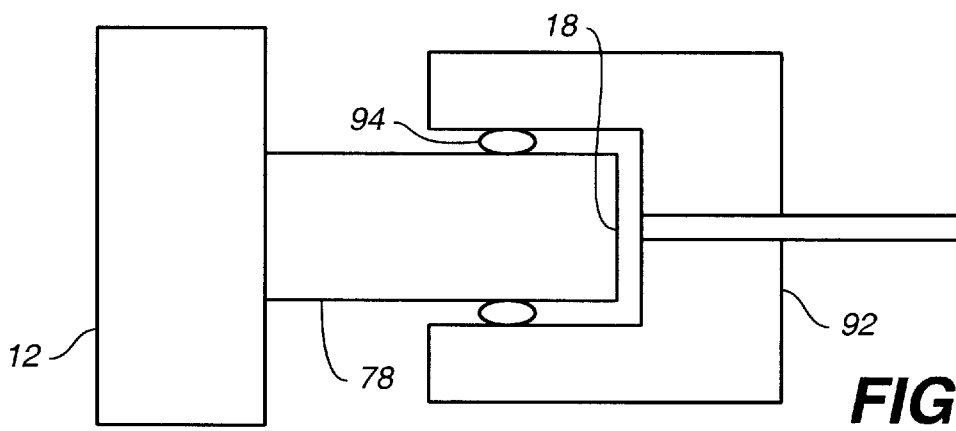
FIG._6

METHOD FOR FILLING ACOUSTIC IMPLANTABLE TRANSDUCERS

CROSS REFERENCE TO RELATED APPLICATION

This patent application is a continuation-in-part of U.S. patent application Ser. No. 09/688,292 filed Oct. 13, 2000.

CLAIM OF PROVISIONAL APPLICATION RIGHTS

The patent application of which this is a continuation-in-part that is identified in the immediately preceding paragraph, and this continuation-in-part patent application both claim the benefit of U.S. Provisional Patent Application No. 60/159,154 filed on Oct. 13, 1999.

BACKGROUND OF THE INVENTION

1. Field of the Invention

The present invention relates generally to methods employed for successfully fabricating, testing and transporting a minute transducer that includes a liquid filled chamber which has thin membranes forming portions of the chamber's wall.

2. Description of the Prior Art

U.S. Pat. No. 5,772,575 ("the '575 patent") that issued Jun. 30, 1998, on a patent application filed by S. George Lesinski and Armand P. Neukermans describes transducers used for a fully implantable hearing aid system. As disclosed in the '575 patent, the fully implantable hearing aid system's transducer cannot exceed 1.2 mm in diameter, and includes a hollow chamber having two (2) walls that are formed by thin, flexible membranes.

The hollow chamber within these implantable transducers must be completely filled with a liquid material while concurrently excluding gas bubbles (except as such bubbles may be deliberately placed within the hollow chamber to provide a special low pass acoustic filter). In general, the presence of even a small bubble inside the hollow chamber may render the transducer ineffective because it prevents efficient liquid displacement transfer from a first thin membrane, i.e. an input membrane, to a second thin membrane, i.e. an output membrane. Because small orifices and complicated shapes are involved in fabricating an implantable transducer that cannot have a diameter greater than 1.2 mm, and because the surface to volume ratio within the hollow chamber is large, extremely small bubbles may be easily trapped within the hollow chamber during filling.

In addition to technical difficulties associated with bubble free filling of implantable transducers as summarized above, the thin membranes combined with the liquid within the transducer's hollow chamber presents additional technical difficulties while testing the transducers, and while they are being shipped. For example, the United States Food and Drug Administration ("FDA") requires that class III type implantable devices be tested at an elevated temperature to accelerate failure of defective devices. Heating a liquid filled implantable transducer may cause the liquid within the hollow chamber to expand more rapidly than the rest of the transducer. Consequently, heating an implantable transducer that is filled with water surely increases the pressure of liquid within the hollow chamber, and may rupture or plastically deform one or both of the membranes. Similarly, a possibility exists that unprotected implantable transducers may be damaged during shipping if they are exposed to extreme temperatures.

BRIEF SUMMARY OF THE INVENTION

An object of the present invention is to provide methods for filling transducers of a fully implantable hearing aid system with liquid regardless of the liquid's vapor pressure.

Another object of the present invention is to provide a method that prevents damaging liquid filled transducers of a fully implantable hearing aid system while testing them at elevated temperatures.

Another object of the present invention is to provide methods that prevent damaging liquid filled transducers of a fully implantable hearing aid system while they are being transported.

The transducer of the fully implantable hearing aid system has a body:
1. which surrounds the hollow chamber and includes at least one thin membrane that forms at least a portion of a wall of the hollow chamber; and
2. at least one passage having:
   a. an exit that couples the passage to the hollow chamber; and
   b. an entrance that is located distal from the hollow chamber for communicating via the passage with the hollow chamber from outside the implantable transducer, Bubble free filling of the hollow chamber with a high vapor pressure liquid is effected by first establishing a seal around the entrance of the passage. Then, while protecting the thin membrane from damage, evacuating the hollow chamber through the passage by applying vacuum to the entrance thereof. After the hollow chamber has been evacuated, bubble free filling of the hollow chamber with a high vapor pressure liquid is effected by:
1. cooling the body of the implantable transducer to establish a temperature gradient therealong at least a portion of which has a temperature that is below a dew point of the high vapor pressure liquid; while concurrently
2. introducing into the entrance of the passage a vapor of the liquid.

Thus, upon condensation of the vapor within the hollow chamber of the implantable transducer, the hollow chamber becomes filled with the liquid without creating a bubble within the hollow chamber.

These and other features, objects and advantages will be understood or apparent to those of ordinary skill in the art from the following detailed description of the preferred embodiment as illustrated in the various drawing figures.

BRIEF DESCRIPTION OF THE DRAWINGS

FIGS. 1A and 1B are schematic diagrams that respectively illustrate an arrangement for bubble-free filling with low vapor pressure liquid a hollow chamber within an implantable transducer.

FIGS. 2A and 2B are schematic diagrams that respectively illustrate an arrangement for individually filling chambers with a high vapor pressure liquid which uses vapor condensation with alternative techniques for protecting a thin membrane during evacuation of the implantable transducer's chamber.

FIG. 3 is a schematic diagram that illustrates an implantable transducer which includes supports located within the hollow chamber within the implantable transducer for supporting the thin membrane during evacuation of the chamber.

FIG. 4 is a schematic diagram that illustrates a controlled pressure oven that encloses an implantable transducer.

FIG. 5 is a schematic diagram that illustrates an arrangement suitable for safely transporting implantable transducers.

FIG. 6 is a schematic diagram that illustrates an alternative arrangement for protecting the implantable transducer's thin membrane during transportation.

DETAILED DESCRIPTION

FIG. 1A illustrates a vacuum chamber 10 which encloses several implantable transducers 12. Each of these implantable transducers 12 respectively includes a body 14 that has a thin input membrane 16 and output membrane 18 which are located on opposite sides of a hollow chamber 22. A hollow filling tube 24 depends beneath each of the bodies 14, and a hollow appendage 26, which is long and closed at an end 28 furthest from the body 14, project upward above each of the bodies 14. The filling tubes 24 and the appendages 26 may be formed from metal tubes which are readily swaged to hermetically seal the chamber 22. The ends 28 of the appendages 26 are at the highest points within the vacuum chamber 10. The vacuum chamber 10 also encloses a container 32 that holds a low vapor pressure liquid 34 (e.g. silicone oil) with which the chambers 22 of each of the implantable transducers 12 will be filled.

Initially, gas is evacuated from the vacuum chamber 10. If necessary, the implantable transducers 12 may be heated with infrared red lamps to purge moisture from the chambers 22, the filling tubes 24 and the appendages 26. This procedure also outgasses the liquid 34 in the container 32, such that it can, in principle, absorb small amounts of gas later upon cooling. The elongated filling tubes 24 and appendages 26 may require a substantial out-gassing interval to remove all adsorbed gases. The pressure within the vacuum chamber 10 should preferably approach $10^{-5}$ Torr.

Preferably the chamber 22 within the implantable transducer 12 is configured to avoid places that will trap gas bubbles. That is, interior surfaces of the implantable transducers 12 are configured such that entering liquid 34 entirely sweeps any gas remaining within the implantable transducer 12 in front of the liquid 34, without trapping gas in any cavities. Interior surfaces of the implantable transducers 12 are polished to the maximum extent possible in an attempt to eliminate bubble formation. Before filling the chamber 22 with the liquid 34, vapor of a surfactant material may be introduced into the vacuum chamber 10 to coat interior surfaces of the implantable transducers 12 everywhere thereby lowering the surface tension of the liquid 34 when it enters the implantable transducers 12.

The container 32 is then tipped so the liquid 34 spills out to submerge open ends 38 of the filling tubes 24. The vacuum within the vacuum chamber 10 is then very slowly reduced preferably by admitting into the vacuum chamber 10 a gas that is poorly absorbed by the liquid 34. A difference thus established between the pressure within the vacuum chamber 10 and that within the implantable transducers 12 drives the liquid 34 up the filling tubes 24 to fill the chambers 22 of the implantable transducers 12. The pressure within each implantable transducer 12 is initially extremely low, and gradually increases as the liquid 34 intrudes thereinto. The liquid drives any residual gas within the implantable transducer 12 into the top of the appendage 26. Therefore it is advantageous to raise the pressure within the vacuum chamber 10 very slowly.

During filling of the chamber 22 with the liquid 34, any entrapped bubbles, in areas not swept clean by the entering liquid, will be markedly compressed in the ratio of the pressure within the vacuum chamber 10 when filling begins to the pressure when filling ends. The maximum pressure that needs to be applied to fill the appendages 26 to their top approaches the hydrostatic pressure due to the height of the liquid 34 within the implantable transducers 12 above the surface of the liquid 34 at the bottom of the vacuum chamber 10. Since for the minute implantable transducers 12 this height is approximately 1 cm, any bubbles will be compressed volumetrically in the ratio of about 760, and will be very small when the final pressure within the vacuum chamber 10 reaches 1 atmosphere. Any residual gas remaining within the implantable transducers 12 that does not form a bubble should collect at the top of the appendages 26 as illustrated in FIG. 1B. This section of each of the appendages 26 may be swaged off and also the filling tubes 24. In this way each implantable transducer 12 becomes hermetically sealed and virtually gas free.

If the liquid 34 for filling the implantable transducer 12 has a high vapor pressure, e.g. water, alcohol, etc., the method described in connection with FIGS. 1A and 1B is unsuitable for filling the implantable transducer 12. FIG. 2A illustrates schematically an arrangement that is suitable for filling the implantable transducer 12 with a high vapor pressure liquid 34. Similar to FIGS. 1A and 1B, the implantable transducer 12 illustrated in FIG. 2A includes a thin input membrane 16 and output membrane 18, and may also include a transducer not illustrated in FIGS. 2A and 2B. The filling tube 24 of the implantable transducer 12, which connects to a vacuum system 44, includes an exit 42 located at the chamber 22 of the implantable transducer 12.

A wall 46 surrounds the implantable transducer 12 together with an encircling O-ring 48 which seals with and establishes a vacuum tight enclosure around the implantable transducer 12. A cooler 52, also enclosed within the wall 46, makes intimate thermal contact with the implantable transducer 12. The cooler 52 may employ thermoelectric cooling or any other suitable technique. Preferably, the wall 46, the implantable transducer 12 and the cooler 52 are arranged to establish a substantial temperature gradient along the implantable transducer 12, with the portion of the implantable transducer 12 furthest from the exit 42 that contacts the cooler 52 being the coldest.

To fill the chamber 22 with high vapor pressure liquid 34, first an entrance 54 of the filling tube 24 is inserted into a port 56 of the vacuum system 44 with an O-ring 58 sealing between the filling tube 24 and the port 56 so the chamber 22 can be evacuated. Concurrently, an approximately equal vacuum is applied to a chamber 59 that is located between the implantable transducer 12 and the surrounding wall 46 so pressures on opposite sides of the input membrane 16 and the output membrane 18 are equal while the chamber 22 is evacuated. Evacuation of the chamber 22 continues in this way until the pressure within the chamber 22 reaches approximately $10^{-5}$ Torr. Upon reaching that low pressure, the composition of gases within the vacuum system 44 changes slightly by introducing into the vacuum system 44 a partial vapor pressure of a surfactant material. Because of the very low pressure, atoms of the surfactant diffuse into the chamber 22 quickly. In this way interior surfaces of the implantable transducer 12 become coated everywhere with surfactant to thereby lower the surface tension of the liquid 34 when it enters the implantable transducer 12 thus permitting the liquid 34 to readily wet interior surfaces of the implantable transducer 12.

After the surfactant has diffused into the chamber 22, the composition of the gases within the vacuum system 44 changes again upon introduction of a vapor of the high vapor pressure liquid 34 thereinto, and the pressure both within the vacuum system 44 and the wall 46 increases slightly, for example to a few Torr. The cooler 52 then lowers the temperature of the chamber 22, preferably establishing the temperature gradient with the portion of the implantable transducer 12 furthest from the exit 42 that contacts the cooler 52 being the coldest. When the temperature within the chamber 22 drops below the dew point for the vapor pressure of the liquid 34 within the vacuum system 44, the liquid 34 condenses inside of the implantable transducer 12, preferably at the bottom. By gradually reducing the temperature of the implantable transducer 12 while maintaining it above the freezing temperature of the liquid 34, and/or by increasing the vapor pressure of the liquid 34 within the vacuum system 44, any vapor bubbles which may form within the chamber 22 condense into the liquid 34. During filling of the implantable transducer 12, temperatures everywhere else are maintained above the dew point established for vapor pressure of the liquid 34 within the vacuum system 44.

FIG. 2B schematically illustrates a similar concept for filling the implantable transducer 12 with the liquid 34. However, the configuration depicted in FIG. 2B omits the wall 46. Instead, outside surfaces of the input membrane 16 and the output membrane 18 are covered with a quantity of a material 62 that adheres to them and that is easily removed, e.g. wax. The material 62 supports the input membrane 16 and the output membrane 18 during evacuation of the chamber 22. Other than for omitting the wall 46 and adding the material 62, the remainder of the procedure for filling the implantable transducer 12 illustrated in FIG. 2B is similar to that described above in connection with FIG. 2A.

As illustrated in FIG. 3, some configurations for the implantable transducer 12 permit supporting the input membrane 16 during evacuation of the chamber 22 by disposing supports 72 adjacent thereto. The implantable transducer 12 illustrated in FIG. 3 is preferably fabricated from a silicon wafer 74 with etched supports 72 formed on an interior surface of the body 14 at numerous small points to support the input membrane 16 during evacuation. In the assembled implantable transducer 12, the supports 72 are located near to but not contacting the input membrane 16. In the configuration of the implantable transducer 12 depicted in FIG. 3, the input membrane 16 carries a transducer 76 on a surface thereof which is furthest from the supports 72. A tube 78, included in the implantable transducer 12 and preferably made from Ti, projects outward from the wafer 74. The output membrane 18 seals the end of the tube 78 furthest from the input membrane 16.

During evacuation of the implantable transducer 12, the supports 72 restrict inward deflection of input membrane 16 to a few microns. Restricting inward deflection of the input membrane 16 to this small amount provides sufficient deflection of the input membrane 16 for normal operation of the implantable transducer 12, while also adequately protecting the input membrane 16 and the transducer 76 from damage during vacuum filling of the implantable transducer 12 with the liquid 34.

Accelerated life-testing mandated by the FDA for class III type implantable devices requires raising the device's temperature to stimulate accelerated device failure. For the implantable transducer 12 filled with the liquid 34, elevated temperature presents a problem since volumetric expansion of a liquid 34 such as water is 200 PPM versus 25–30 PPM for a body made of titanium such as the tube 78 illustrated in FIG. 3. Consequently, raising the temperature of a water filled implantable transducer 12 increases the pressure within the chamber 22, and may rupture or plastically deform the input membrane 16 or the output membrane 18. To prevent damaging the implantable transducers 12 in this way, as illustrated in FIG. 4 the implantable transducer 12 may be enclosed in a pressure oven 82 so the pressure outside the implantable transducer 12 increases in the same manner as pressure within the implantable transducer 12 rises.

Likewise, during transportation the implantable transducer 12 may be exposed to elevated storage temperatures that might damage it due to the expansion of the liquid 34 within the implantable transducer 12. As illustrated in FIG. 5, to prevent damage during transportation the implantable transducers 12 may be enclosed in a can 86 which is made from a material (e.g. titanium) that has the same relative expansion as the implantable transducer 12. The can 86 is completely filled with liquid (possibly the same liquid as that filling the implantable transducer 12). Hence, as the temperature of the can 86 changes pressures inside and outside of the implantable transducers 12 remain in equilibrium thereby preventing damage to the implantable transducers 12 within the can 86.

Alternatively, as illustrated in FIG. 6 an end of the implantable transducer 12 carrying the output membrane 18 may be covered by a protective cover 92. An O-ring 94 seals the cover 92 to the tube 78, and sealed space between the tube 78 and the cover 92 is pressurized to prevent inadvertently damaging the implantable transducer 12 during transportation.

Although the present invention has been described in terms of the presently preferred embodiment, it is to be understood that such disclosure is purely illustrative and is not to be interpreted as limiting. Consequently, without departing from the spirit and scope of the invention, various alterations, modifications, and/or alternative applications of the invention will, no doubt, be suggested to those skilled in the art after having read the preceding disclosure. Accordingly, it is intended that the following claims be interpreted as encompassing all alterations, modifications, or alternative applications as fall within the true spirit and scope of the invention.

What is claimed is:

1. A method for bubble-free filling of an implantable transducer with a liquid, the implantable transducer including:
    a body which surrounds a hollow chamber that must be filled with the bubble-free liquid, the body including at least one thin membrane that forms at least a portion of a wall of the hollow chamber; and
    at least one passage formed in the body of the implantable transducer having:
        an exit that couples the passage to the hollow chamber of the implantable transducer; and
        an entrance that is located distal from the hollow chamber for communicating via the passage with the hollow chamber from outside the implantable transducer,
the implantable transducer filling method comprising the steps of:
    establishing a seal around the entrance of the passage;
    while protecting the thin membrane of the body of the implantable transducer from damage, evacuating the hollow chamber through the passage by applying vacuum to the entrance thereof;
    while cooling the body of the implantable transducer to establish a temperature gradient therealong at least a portion of which has a temperature that is below a dew point of the liquid, introducing into the entrance of the passage a vapor of the liquid whereby, upon condensation of the vapor within the hollow chamber of the implantable transducer, the hollow chamber becomes filled with the liquid without creating a bubble within the hollow chamber.

2. The method of claim 1 wherein cooling the body of the implantable transducer progressively lowers the temperature further below the dew point as the hollow chamber fills with the liquid.

3. The method of claim 1 wherein the thin membrane of the body of the implantable transducer is protected from damage by:

establishing a vacuum tight enclosure around the implantable transducer; and applying a vacuum within the vacuum tight enclosure around the implantable transducer that is approximately equal to vacuum within the hollow chamber so pressures on opposite sides of the thin membrane are substantially equal while the hollow chamber is evacuated.

4. The method of claim 1 wherein the thin membrane of the body of the implantable transducer is protected from damage by adhering an easily removable material to an outside surface of the thin membrane.

5. The method of claim 1 wherein, before introducing the vapor of the liquid into the entrance of the passage, introducing a partial vapor pressure of a surfactant material into the entrance of the passage so atoms of the surfactant material diffuse into the hollow chamber to thereby lower surface tension of the liquid when the liquid enters the hollow chamber thus permitting the liquid to readily wet interior surfaces of the implantable transducer.

* * * * *